(12) United States Patent
Hossick-Schott et al.

(10) Patent No.: US 7,491,246 B2
(45) Date of Patent: Feb. 17, 2009

(54) CAPACITOR ELECTRODES PRODUCED WITH ATOMIC LAYER DEPOSITION FOR USE IN IMPLANTABLE MEDICAL DEVICES

(75) Inventors: Joachim Hossick-Schott, Minneapolis, MN (US); Naim S. Istephanous, Roseville, MN (US); John D. Norton, New Brighton, MN (US); Anthony W. Rorvick, Champlin, MN (US); Richard W. A. Francis, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 76 days.

(21) Appl. No.: 11/278,307

(22) Filed: Mar. 31, 2006

(65) Prior Publication Data

US 2007/0236867 A1 Oct. 11, 2007

(51) Int. Cl.
*H01L 21/00* (2006.01)
(52) U.S. Cl. .................................................. 29/25.01
(58) Field of Classification Search ..... 29/25.01–25.03; 257/296
See application file for complete search history.

(56) References Cited

U.S. PATENT DOCUMENTS

| | | | |
|---|---|---|---|
| 5,980,977 A | 11/1999 | Deng et al. | |
| 6,141,205 A | 10/2000 | Nutzman et al. | |
| 6,551,873 B2 | 4/2003 | Park et al. | |
| 6,551,893 B1 | 4/2003 | Zheng et al. | |
| 2002/0055242 A1 | 5/2002 | Uhlenbrock et al. | |
| 2003/0141193 A1 | 7/2003 | Hossick-Schott | |
| 2004/0077142 A1 | 4/2004 | Chao et al. | |
| 2004/0110348 A1 | 6/2004 | Ahn et al. | |
| 2004/0110391 A1 | 6/2004 | Ahn et al. | |
| 2005/0032325 A1 | 2/2005 | Bhat et al. | |
| 2005/0045092 A1* | 3/2005 | Wu et al. | 117/92 |
| 2005/0194628 A1* | 9/2005 | Kellar et al. | 257/296 |
| 2005/0254199 A1 | 11/2005 | Liu et al. | |
| 2007/0014919 A1* | 1/2007 | Hamalainen et al. | 427/248.1 |

FOREIGN PATENT DOCUMENTS

WO    WO 2006/014753 A1 *    2/2006
WO    WO2006014753    2/2006

* cited by examiner

*Primary Examiner*—Zandra Smith
*Assistant Examiner*—Paul E Patton
(74) *Attorney, Agent, or Firm*—Carol F. Barry

(57) ABSTRACT

An electrolytic capacitor cell for use in implantable medical devices and associated method for manufacture are provided. The capacitor cell includes an electrode substrate having a dielectric layer formed thereon by atomic layer deposition. In various embodiments, the dielectric layer includes an oxide of one or more valve metals.

25 Claims, 12 Drawing Sheets

CAPACITOR ELECTRODES PRODUCED WITH ATOMIC LAYER DEPOSITION FOR USE IN IMPLANTABLE MEDICAL DEVICES

RELATED APPLICATIONS

This application is related to, and claims the benefit of, U.S. patent application Ser. No. 11/343,356 filed Jan. 31, 2006 entitled "Capacitors Based on Valve Metal Alloys for Use in Medical Devices", which is incorporated herein by reference in its entirety.

TECHNICAL FIELD

The invention relates generally to capacitors used in implantable medical devices and, in particular, to an electrode produced using atomic layer deposition for use in an implantable medical device capacitor.

BACKGROUND

Many implantable medical devices (IMDs) that are used to treat or monitor patients suffering from a variety of conditions rely on electrochemical cells for providing the energy needed to power the device electronics and generate therapeutic electrical stimulation pulses. Examples of such IMDs include implantable pacemakers and implantable cardioverter-defibrillators (ICDs), which are electronic medical devices that monitor the electrical activity of the heart and provide electrical stimulation to one or more of the heart chambers as necessary. Pacemakers deliver relatively low-voltage pacing pulses in one or more heart chambers. ICDs can deliver high-voltage cardioversion and defibrillation shocks in addition to low-voltage pacing pulses IMDs including pacemakers, ICDs, drug pumps, neurostimulators, physiological monitors such as hemodynamic monitors or ECG monitors, typically require at least one battery to power the various components and circuitry used for performing the device functions. Pacemakers and ICDs generally include pulse generating circuitry required for delivering pacing and/or cardioversion and defibrillation pulses, control circuitry, telemetry circuitry, recharge circuitry and other circuitry that require an energy source. In addition to a battery, ICDs include at least one high-voltage capacitor for use in generating high-voltage cardioversion and defibrillation pulses.

IMDs are preferably designed with a minimal size and mass to minimize patient discomfort and prevent tissue erosion at the implant site. Capacitors contribute substantially to the overall size and mass of an ICD. Capacitors for use in an ICD are typically provided with a hermetically-sealed encasement for housing an electrode assembly, including an anode and cathode, an electrolyte, and other components such as a separator, electrode connector feedthroughs and lead wires. The encasement includes a case and a cover that are sealed through joining processes such as laser welding after assembling the cell components within the case.

Factors affecting the performance of electrolytic capacitors include the effective surface area of the anodes and cathodes that can be contacted by the electrolyte, the dielectric constant of the oxide formed on the electrode surface, and the thickness and properties of the dielectric layer. To improve the capacitor cell performance, porous or surface-enhanced electrode substrate materials are used to effectively increase the electrode surface area. For example, flat electrolytic capacitors often include aluminum sheets that are etched or perforated to increase the electrode surface area. Pellet or slug-type electrodes are formed from a valve metal powder that is pressed and formed into a porous substrate.

Typically, an oxide dielectric layer is grown anodically upon exposed surfaces of the electrode when the electrode is immersed in a formation electrolyte. The composition of the oxide layer grown anodically is limited to oxides of the elements found in the electrode substrate. Deposition of a dielectric layer having a composition differing from the substrate composition may be deposited onto an electrode substrate, for example by physical vapor deposition. However, such deposition of a dielectric layer onto a highly structured substrate surface is not likely to achieve uniform coverage of the substrate surface, resulting in defects such as "pin holes". Non-uniform coverage of the substrate surface will result in inferior electrode performance.

DETAILED DESCRIPTION

Figure 1:
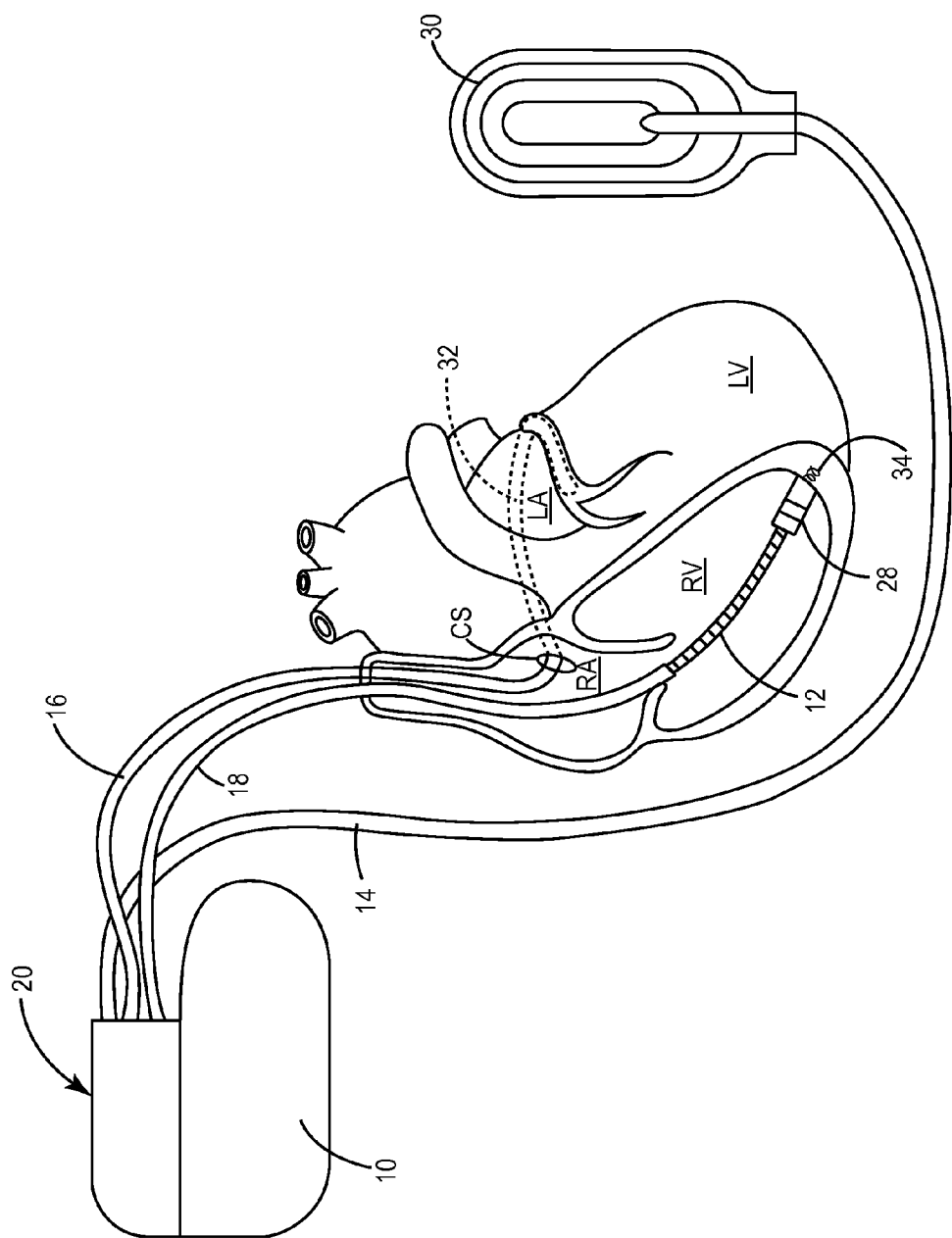
FIG. 1 illustrates one example of an IMD according to one embodiment of the invention.

In the following description, references are made to illustrative embodiments for carrying out the invention. It is understood that other embodiments may be utilized without departing from the scope of the invention. For purposes of clarity, the same reference numbers are used in the drawings to identify similar elements. Unless otherwise noted, drawing elements are not shown to scale.

The present invention is generally directed to providing an electrolytic capacitor cell for use in IMDs having a dielectric layer deposited on an electrode substrate using atomic layer deposition (ALD). A high surface area electrode having a high dielectric constant oxide layer will have enhanced energy density, which may allow the overall cell size, and thus the overall IMD size, to be reduced. Alternatively, the volumetrically more efficient capacitor cell frees space for other components in the IMD for enhancing IMD function or adding new functions.

FIG. 1 illustrates one example of an IMD according to one embodiment of the invention. IMD 10 is embodied as an ICD and is shown with associated electrical leads 14, 16 and 18 and their operative relationship to a human heart. The leads are coupled to IMD 10 by means of multi-port connector block 20, which contains separate connector ports for each of the three leads illustrated.

Lead 14 is coupled to subcutaneous electrode 30, which is intended to be mounted subcutaneously in the region of the left chest. Lead 16 is a coronary sinus lead employing an elongated coil electrode 32 which is located in the coronary sinus and/or great cardiac vein region of the heart. The location of the coronary sinus electrode 32 may be anywhere along the heart from a point within the opening of the coronary sinus (CS) to a point in the vicinity of the left atrial (LA) appendage or left ventricle (LV).

Lead 18 is provided with elongated coil electrode 12 which is disposed in the right ventricle (RV) of the heart. Lead 18 also includes a tip electrode 34 and ring electrode 28 available for pacing and sensing in the RV. While one lead system having a particular electrode arrangement is shown in FIG. 1, numerous lead systems with varying electrode configurations are possible for use with an ICD or other IMDs used for delivering cardiac stimulation pulses.

In the system illustrated, cardiac pacing pulses can be delivered in the right ventricle (RV) between tip electrode 34 and ring electrode 28. Electrodes 28 and 34 can also be employed to sense electrical signals for detecting the heart rhythm. High-voltage defibrillation or cardioversion pulses may be delivered as needed using any of the right ventricular coil electrode 12, coronary sinus coil electrode 32, and subcutaneous patch electrode 30. In some embodiments, the housing of IMD 10 is used as a "case" or "can" electrode in combination with any of the high-voltage electrodes for delivering defibrillation or cardioversion shocks. IMD 10 is merely one example of numerous IMDs that rely on electrochemical cells for powering device electronics or providing the energy needed for generating therapeutic electrical stimulation pulses.

Figure 2:
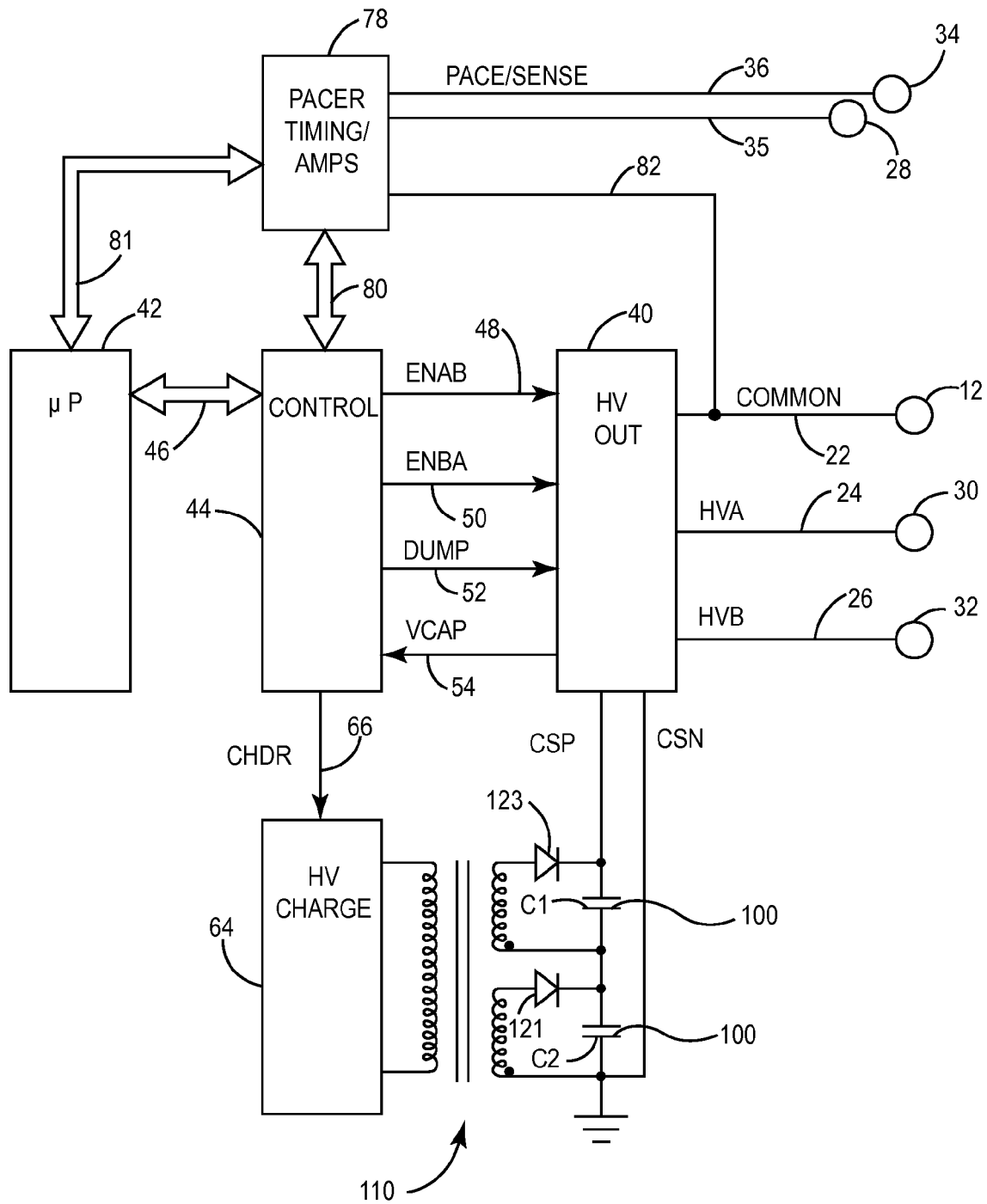
FIG. 2 is a functional block diagram of the IMD 10 shown in FIG. 1.

FIG. 2 is a functional block diagram of one embodiment of IMD 10 illustrating the interconnection of high voltage output circuit 40, high voltage charging circuit 64 and capacitors 100. IMD 10 includes a control system typically in the form of a microprocessor 42, which performs all necessary computational functions within the device. Microprocessor 42 is linked to control circuitry 44 by means of bidirectional data/control bus 46, and thereby controls operation of the high voltage output circuitry 40 and the high voltage charging circuitry 64. On reprogramming of the device or on the occurrence of signals indicative of delivery of cardiac pacing pulses or of the occurrence of cardiac contractions, pace/sense circuitry 78 will awaken microprocessor 42 to perform any necessary mathematical calculations, to perform tachycardia and fibrillation detection procedures and to update the time intervals controlled by the timers in pace/sense circuitry 78.

Control circuitry 44 provides signals to high voltage output circuitry 40. Those signals include control signals, labeled here as ENAB line 48, ENBA line 50, and DUMP line 52 which initiates discharge of the output capacitors 100. VCAP line 54 provides a signal indicative of the voltage stored on the output capacitors 100 to control circuitry 44. High voltage electrodes 12, 30 and 32 illustrated in FIG. 1, above, are shown coupled to output circuitry 40 by means of conductors 22, 24 and 26. For ease of understanding, those conductors are also labeled as "COMMON", "HVA" and "HVB". However, other configurations are also possible. For example, subcutaneous electrode 30 may be coupled to HVB conductor 26, to allow for a single pulse regimen to be delivered between electrodes 12 and 30. During a logic signal on ENAB line 48, a cardioversion/defibrillation pulse is delivered between electrode 30 and electrode 12. During a logic signal on ENBA line 50, a cardioversion/defibrillation pulse is delivered between electrode 32 and electrode 12.

The output circuitry includes one or more capacitors C1 and C2 100, arranged in a capacitor bank, and diodes 121 and 123, used for delivering high-voltage pulses to the electrodes. In FIG. 2, capacitors 100 are illustrated in conjunction with high voltage charging circuitry 64, controlled by the control/timing circuitry 44 by means of CHDR line 66. As illustrated, capacitors 100 are charged by means of a high frequency, high voltage transformer 110. Proper charging polarities are maintained by means of the diodes 121 and 123. VCAP line 54 provides a signal indicative of the voltage on the capacitor bank, and allows for control of the high voltage charging circuitry and for termination of the charging function when the measured voltage equals the programmed charging level.

The capacitor cells 100 include an anode, a cathode, an electrolyte operatively associated with the anode and the cathode, and, in the case of a liquid electrolyte, a separator disposed between the anode and cathode. The separator prevents internal electrical short circuit conditions while allowing sufficient movement of the liquid electrolyte within the cell. The capacitor cells 100 provide the charge necessary to HV output circuitry 40 for generating high voltage defibrillation/cardioversion shocks as needed. As will be described herein, capacitor cells 100 are provided having an ALD deposited dielectric layer on the anodes and/or cathodes included in cells 100.

Pace/sense circuitry 78 includes a sense amplifier used for sensing R-waves. Pace/sense circuitry 78 also includes a pulse generator for generating cardiac pacing pulses and includes timing circuitry for defining pacing intervals, refractory intervals and blanking intervals, under control of microprocessor 42 via control/data bus 80.

Control signals triggering generation of cardiac pacing pulses by pace/sense circuitry 78 and signals indicative of the occurrence of R-waves, from pace/sense circuitry 78 are communicated to control circuitry 44 by means of a bidirectional data bus 80. Pace/sense circuitry 78 is coupled to tip electrode 34 and ring electrode 28, illustrated in FIG. 1, by respective conductors 35 and 36. Pace/sense circuitry 78 may also be coupled to right ventricular coil electrode 12 by a conductor 82, allowing for sensing of R-waves between electrodes 34 and 28 and for delivery of pacing pulses between electrodes 34 and 28. All of these functions are powered by a low voltage battery cell appropriately coupled to the various device components, which are generally configured on a hybrid circuit board.

Figure 3A:
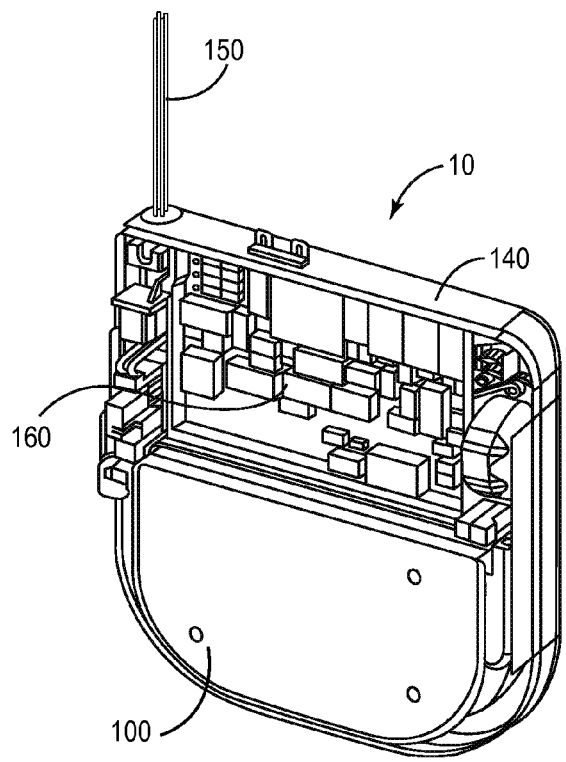
FIG. 3A is a sectional view of a capacitor cell placed within a housing of an IMD.

FIG. 3A is a sectional view of a capacitor cell 100 placed within a housing 140 of IMD 10. Electronic components included in IMD 10, such as those represented in the functional block diagram of FIG. 2, are included in an electronics module 160. Electronics module 160 can assume a wide variety of forms and generally includes a circuit board maintaining and interconnecting electrical components. The exact composition of electrical components can vary from application to application but is generally configured to perform various sensing or monitoring routines, as well as to store data related to operation of IMD 10, such as therapy delivery operations. Electronics module 160 is electrically coupled to stimulation and sensing electrodes through feed-through 150, extending through device housing 140.

Capacitor 100 is typically a high-voltage capacitor capable of storing energy using a low-voltage battery as a charge source. At an appropriate time, as controlled by electronics module 160, capacitor 100 is discharged. In the case of an ICD, capacitor 100 is discharged through selected electrodes for delivering a high-voltage cardioversion or defibrillation pulse to a patient's heart. Capacitor 100 may include multiple capacitors connected electrically in series by interconnections in electronics module 160. In different embodiments, IMD 10 may include multiple capacitors arranged in any configuration suitable for containment within IMD 10 and connection to electronics module 160. Multiple capacitors may be provided with identical dimensions to allow stacking for volumetric efficiency. In other embodiments, multiple capacitors may be provided with different sizes, shapes and chemistry. It is expected that reformation of capacitor 100 may be needed after periods of inactivity to maintain charging efficiency.

Figure 3B:
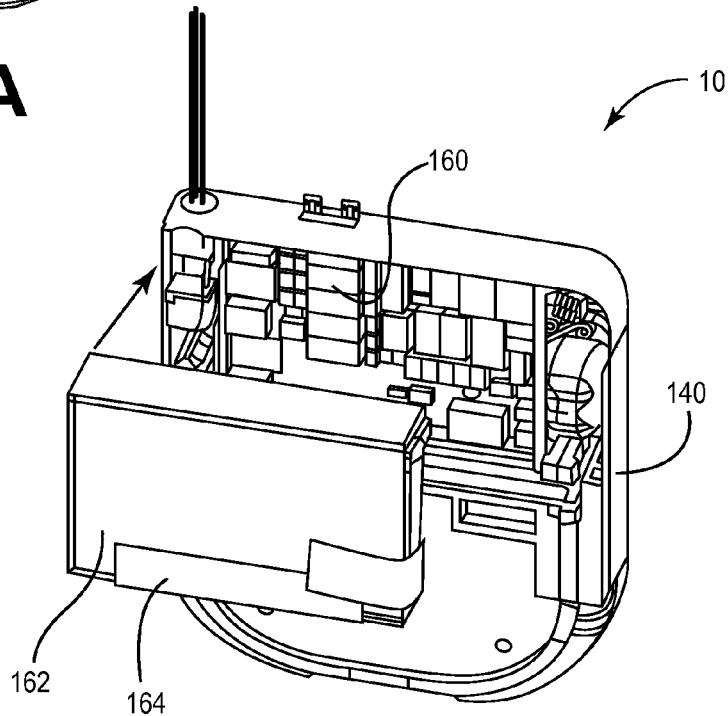
FIG. 3B shows a battery being placed in an IMD housing.

FIG. 3B shows a battery 162 having insulator 164 disposed around battery 162 prior to placing it IMD housing 140. Battery 162 provides the electrical energy required to charge and re-charge capacitor 100, and also powers electronics module 160.

Figure 4A:
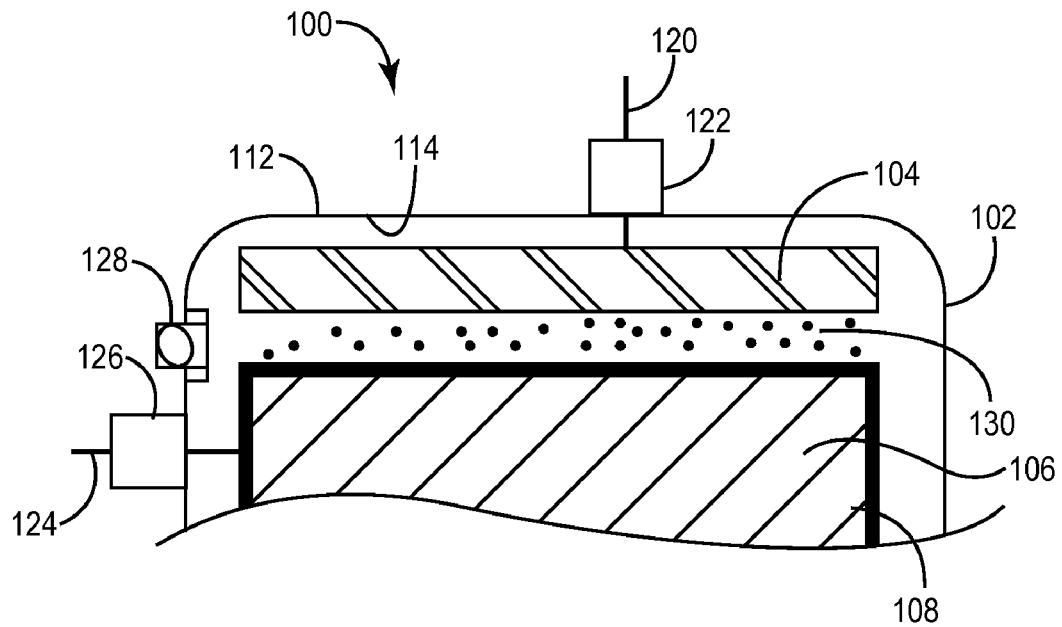
FIG. 4A is a partial, cross-sectional view of an electrolytic capacitor cell according to one embodiment of the invention.

FIG. 4A is a partial, cross-sectional view of an electrolytic capacitor according to one embodiment of the invention. Capacitor 100 is embodied as a high energy density capacitor included in IMD 10 as shown in FIGS. 2 and 3A. Cell 100 includes an encasement 102 for encasing the internal components of the cell. Encasement 102 is generally constructed from a corrosion resistant material such as titanium or an alloy thereof or stainless steel. Encasement 102 may be constructed from other materials including other corrosion resistant metals or alloys, polymeric materials and ceramic materials. Encasement 102 is commonly hermetically sealed, particularly when cell 100 is used in an IMD. Encasement 102 may be provided having a generally prismatic geometry or a contoured shape tailored for a particular application and generally includes a case with a substantially flat cover. The case may be a shallow-drawn or deep-drawn case with the cover typically welded to the case to form a hermetic seal. Examples of encasements used to enclose electrochemical cells for use in implantable medical devices are generally described in U.S. Pat. No. 6,141,205 (Nutzman, et al.). Encasement 102 may alternatively be provided with a "clamshell" design having a two halves that close together to form a sealed encasement.

A cathode 104 and anode substrate 106 are disposed within encasement 102. In the illustrative embodiment shown in FIG. 4A, the anode substrate 106 is provided with a dielectric layer 108 formed thereon using ALD methods, alone or in combination with other methods for forming dielectric films. In various embodiments of the invention, an electrolytic capacitor cell includes at least one electrode having a dielectric layer deposited on a substrate material using ALD. Accordingly, the anode and/or cathode may be formed using ALD.

Anode substrate 106 is fabricated from a conductive material capable of withstanding high temperatures (on the order of 200 to 500 degrees Celsius) experienced during the ALD process. Anode substrate 106 is typically fabricated from a valve metal (aluminum, niobium, titanium, tantalum, zirconium, etc.) or a valve metal alloy, including multi-phase alloys, provided in any suitable form including foils, powders or grown dendritic structures. For example, anode substrate 106 is formed as a pellet or slug structure fabricated from a pressed and formed valve metal or valve metal alloy powder.

The anode substrate 106 and/or cathode 104 may be surface-area enhanced to increase the available conductive surface area. Methods for enhancing the surface area of anode substrate 106 or cathode 104 include chemical etching and mechanical roughening. For example, anode substrate 106 may be an etched foil formed from a valve metal or valve metal alloy. Alternatively, anode substrate 106 may be a porous slug having a complex surface and interior features such as cavities or through-holes as described in U.S. Pat. Application Pub. No. 2004/0134874, incorporated herein by reference in its entirety.

Any material having the characteristics desired for a particular application, such as ductility, mass, dielectric constant, and surface area may be used for anode substrate 106 as long as the material withstands the temperatures experienced during ALD processes. In some embodiments, anode substrate 106 may be provided as a porous or non-porous ceramic material. A ceramic material may be coated with a conductive coating, for example by sputtering one or more conductive metal material. The conductive coating may be surface enhanced by etching or other methods, particularly when a non-porous ceramic substrate material is used. The dielectric layer 108 is then deposited by ALD on the conductive coating. Embodiments of the invention, therefore, include ceramic electrode substrate configurations, including multi-layered configurations, in which a dielectric layer is formed thereon using ALD.

The dielectric layer 108 includes one or more oxides deposited by ALD. The composition of dielectric layer 108 is independent of the composition of anode substrate 106. For example, anode substrate 106 may be formed from a single valve metal, such as tantalum or titanium, and the dielectric layer 108 may be formed having a mixed oxide composition that may or may not contain oxides of tantalum or titanium. It is generally expected that dielectric layer 108 will include one or more metal oxides, however non-metal oxides deposited by atomic layer deposition, such as carbon-based oxides are considered to be within the scope of the present invention.

During an ALD process for applying dielectric layer 108, anode substrate 106 is placed in a deposition chamber. The dielectric layer is deposited by rapid succession of gas pulses which form an oxidized atomic monolayer in two step cycles which include 1) depositing a monolayer of the precursor source material, and 2) oxidizing the monolayer with an oxidant source material. For example, a precursor source material may be $ZrCl_4$ and the oxidant source material may be water for forming zirconium oxide monolayers.

The dielectric layer 108 is deposited layer by layer to a desired thickness by controlling the number of cycles applied for building up one atomic monolayer at a time. The structure (amorphous or crystalline) and thickness of dielectric layer 108 will depend on the particular application and relate to the desired energy density, volume, voltage, current, energy output and other capacitor cell requirements of the particular application.

Dielectric layer 108 applied using ALD methods is a conformal coating, providing uniform coverage of the anode substrate 106, even when anode substrate 106 is provided as a porous or surface-enhanced substrate having a high aspect ratio. As such, capacitor cell performance is enhanced by providing a high surface area electrode with a uniform, conformal dielectric coating.

The dielectric coating may be applied using a standard ALD deposition chamber. A standard chamber includes a vessel that is continuously pumped and held under vacuum.

Precursor source and oxidant source materials are heated to a desired temperature in valve-sealed compartments included in the chamber. Rapid opening and closing of the valves according to a computer-controlled protocol generates precursor gas pulses having a defined length and particle content. The electrode substrate material is positioned in the flight path of the gas pulses such that a coating is applied layer by layer.

When applying a dielectric layer to a highly porous electrode substrate, other ALD chamber configurations may be used to promote uniform deposition of the dielectric layer. For example, a porous electrode substrate may be placed between two chambers, each pumped separately so as to generate a pressure differential between the two chambers, wherein pressure in the first chamber is greater than pressure in the second chamber. Gas pulses traveling from the first chamber into the second chamber are forced to pass through the porous electrode substrate positioned between the two chambers, potentially improving the uniformity of the coating along the interior portions of the porous electrode substrate.

The electrode substrate temperature can also be controlled to influence the physical structure of the deposited oxide (amorphous or crystalline), which in turn affects the properties of the dielectric layer. Alternatively, an amorphous structure of a dielectric layer can be altered to a crystalline form by applying heat (annealing) during post-processing methods.

As indicated above, the composition of the dielectric layer 108 can be selected independent of the substrate composition since the ALD process produces a uniform, conformal dielectric layer. As such, the dielectric layer may be a doped composition including elements for enhancing the electrode performance. For example, the composition of the dielectric layer 108 may be selected to provide a high dielectric constant or provide other enhancements of cell performance.

Layer-by-layer growth of two or more different metal oxides may be accomplished by applying two or more precursor source materials, each including a different metal. In one example embodiment, a mixed valve metal oxide dielectric layer including oxides of Al and Ti is deposited by ALD using the precursor source materials $AlCl_3$ and $TiCl_4$. Oxygen is supplied by subsequent water vapor pulses. A mixed oxide dielectric layer is expected to improve the cell energy density. The dielectric constant of a mixed valve metal oxide dielectric layer is expected to be greater than that of dielectric layers of similar thickness formed from a single valve metal oxide.

Dielectric layer 108 provided as a mixed oxide dielectric layer includes a combination of two or more metal oxides, including, but not limited to, any combination of tantalum oxide, niobium oxide, aluminum oxide, chromium oxide, zirconium oxide, zinc oxide, vanadium oxide, hafnium oxide, and/or titanium oxide. For example, a mixed oxide dielectric layer may include, but is not limited to, $Nb_xAl_yO_z$, $Ta_xTi_yO_z$, or $Nb_xTa_yO_z$.

Figure 4B:
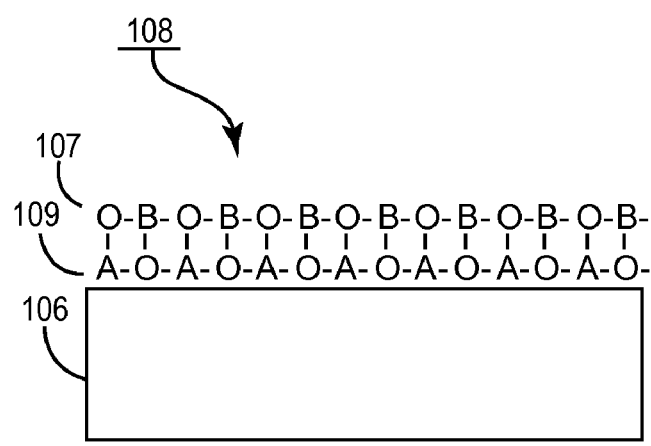
FIG. 4B is a schematic diagram of a mixed oxide dielectric layer alternatively formed by stacking atomic monolayers deposited using different precursor source materials

FIG. 4B is a schematic diagram of a mixed oxide dielectric layer alternatively formed by stacking atomic monolayers deposited using different precursor source materials. The different precursor source materials include different valve metals or valve metal alloys and are alternated during the deposition process to form any variable number of layers of each material. Such mixed, stacked oxide layers may include alternating monolayers 107 and 109 formed from two different metal oxides, $A_xO_y$ and $B_xO_y$. For example, mixed stacked oxide layers may include $Ta_2O_5/Nb_2O_5$, $Al_2O_3/TiO_2$, $Al_2O_3/Ta_2O_5$, $Ta_2O_5/HfO_2$, and $Ta_2O_5/ZrO_2$. Furthermore, a mixed oxide dielectric may be formed including stacked monolayers of a metal oxide and a mixed metal oxide such as $Nb_xTa_yO_z/$ $ZrO_2$. It is recognized that numerous dielectric layer compositions may be formed using ALD methods by selecting different monolayer compositions and variable numbers of monolayers for each composition.

The oxide layer deposited by ALD methods may be treated using any of a number of post processing methods to improve its dielectric properties. For example, a subsequent heat treatment in air or other selected atmospheres may alter the dielectric properties of the coating by altering the oxide structure. A brief post-ALD anodization in a liquid electrolyte may improve the dielectric layer because post-anodization may heal possible pin-holes in the ALD deposited oxide layer. Appropriate valve metal anodizing electrolytes typically include water, an organic solvent such as a glycol, and phosphoric acid, though other anodization electrolytes involving other solvents and organic bases may be also be used.

The anode substrate 106 is electrically coupled to an anode lead 124 that passes through the inner surface 114 and outer surface 112 of encasement 102 via a feed-through 126. Electrical coupling to anode substrate 106 may be achieved using a variety of methods including, for example, ultrasonic welding, resistance welding, laser welding, cold welding, riveting, or staking. Anode lead 124 may be pressed into anode substrate 106 when substrate 106 is pressed and formed from a valve metal powder. The connection method will depend on the particular electrode configuration and number of electrodes, and therefore the number of connection points, used. Examples of electrode connection methods are generally described in U.S. Pat. No. 6,560,089 (Miltich, et al).

The anode lead 124 is electrically isolated from the encasement 102 by a feed-through 126. In one embodiment, the feed-through 126 is constructed of a glass insulator that seals the anode lead 124 to the encasement 102 while maintaining electrical isolation between anode lead 124 and the encasement 102. Other feed-through designs may include epoxy seals, ceramic seals, O-ring compression seals, brazed seals, or riveted compression seals. The feed-through 126, in addition to electrically isolating the anode lead 124 from the encasement 102, substantially prevents material, such as a liquid electrolyte from leaking out of the encasement 102. The feed-through 126 also substantially prevents foreign substances from entering into the encasement 102, thus reducing the likelihood of contamination of the cell internal components.

Cathode 104 may be formed from a metal (e.g., aluminum, titanium, tantalum, niobium, zirconium, etc.) or a metal alloy and its native oxide. The cathode materials may be deposited using ALD or other deposition technologies. In other embodiments, cathode 104 may include a nitride, carbon, carbide, carbon nitride, or titanate coating. Electrochemically active materials including, for example, ruthenium oxide, iridium oxide, vanadium oxide, silver vanadium oxide, and carbon monofluoride are also suitable for fabricating or coating cathode 104.

In some embodiments, cathode 104 is separated (i.e., electrically isolated) from an inner surface 114 of the encasement 102. The cathode 104 is coupled via an electrical connection to a cathode lead 120 that extends through the inner surface 114 and outer surface 112 of the encasement 102. A lead wire may be coupled to cathode 104 using any electrode connection method, for example as described above and in the '089 patent.

The cathode lead 120 is electrically isolated from the encasement 102 by feed-through 122, which may be similar in construction to the anode lead feed-through 126 (as previously discussed). Any feedthrough configuration may be used for enabling electrical coupling to anode substrate 106 and cathode 104.

In other embodiments, the cathode 104 may be physically or electrically connected to encasement 102 such that insulated feedthrough 122 is not required for electrically isolating cathode 104 from encasement 102. Cathode 104 may be formed on an inner surface of encasement 102, and a cathode lead may extend from encasement 102.

The cell 100 generally includes an electrolyte 130 disposed between and in contact with the cathode 104 and anode substrate 106 having dielectric layer 108. Electrolyte 130 provides an ionic charge carrier reservoir for anode 106 and cathode 104. Capacitor 100 may be a wet electrolytic capacitor wherein encasement 102 is filled using fill port 128 with a fluid electrolyte 130. Fill port 128 commonly includes a ferrule and a fill tube through which electrolyte is delivered to the interior of encasement 102. After delivering the electrolyte, a sealing member is typically placed in the fill tube which is then sealed closed using laser welding or another fusion welding technique, though other sealing methods could also be used.

Liquid electrolytes can be based on an inorganic acid, such as sulfuric acid, and/or on solvents such as ethylene glycol or glycol ethers mixed with organic or inorganic acids or salt. The selection of the particular electrolyte 130 may depend on the reactivity of the electrolyte 130 with the materials used for the anode substrate 106, dielectric layer 108 and cathode 104. For example, a sulfuric acid solution used as the electrolyte may be desirable when the anode substrate 106 includes tantalum and/or niobium. In some embodiments, electrolyte 130 may be provided as a solid electrolyte material, as will be further described below. It is recognized that in some embodiments, such as embodiments including a multi-layered ceramic-based electrode assembly, an electrolyte is not necessary.

The anode substrate 106 is shown in FIG. 4A as a porous sintered slug of anode material arranged in operative association with cathode 104 and electrolyte 130. However, the anode substrate 106, having dielectric layer 108 formed thereon, and the cathode 104 can be configured together within encasement 102 according to any suitable arrangement, including multiple-anode configurations. Such arrangements may include a separator disposed between the cathode 104 and anode substrate 106 to prevent short-circuit between the electrodes, particularly when a liquid electrolyte is used. Other configurations may use a solid electrolyte, typically without a separator material. Such configurations include coiled, stacked or layered, and slug type configurations.

When used, separator materials may be layered between anode substrate 106 and cathode 104, or wrapped around one or both of anode substrate 106 and cathode 104. Anode substrate 106 and/or cathode 104 may be enveloped within a pouch of separator material which may be sealed. A separator may be formed from one or more layers of a paper material or impregnated paper material such as kraft paper or manila paper. Separator materials may alternatively be formed from one or more layers of a porous polymeric material, such as polyproplylene or PTFE, or fabric gauze material.

Figure 5:
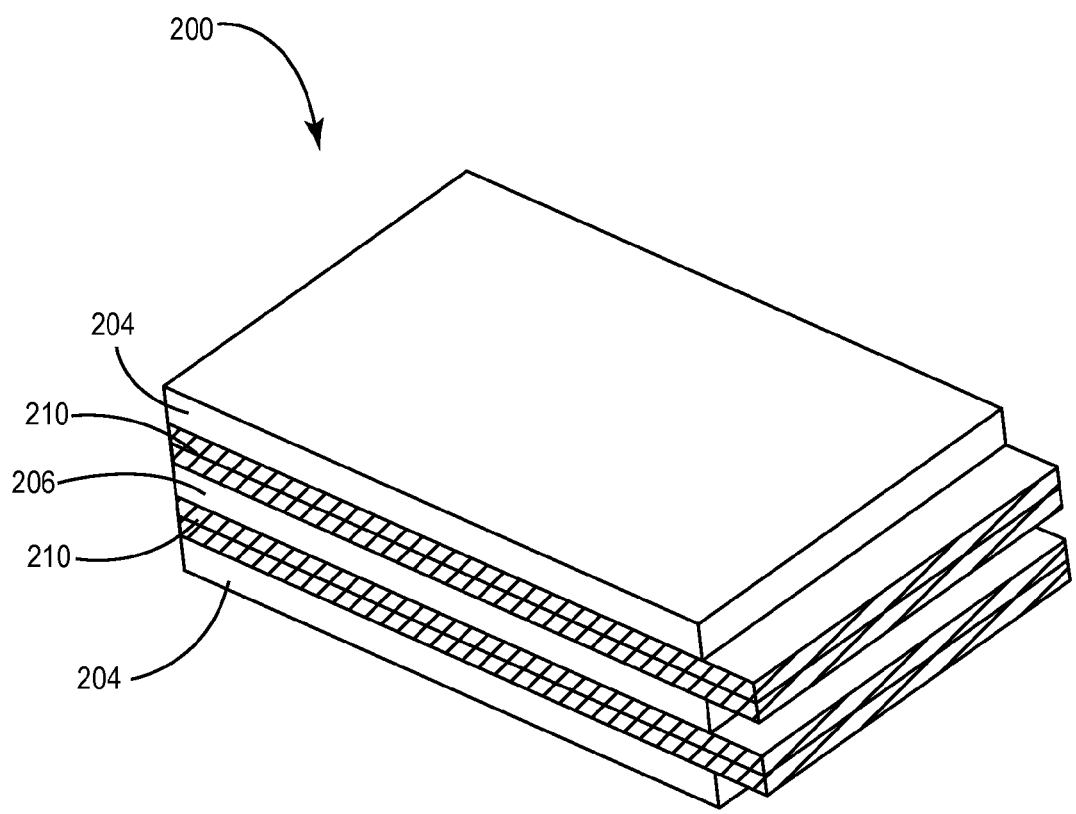
FIG. 5 is a perspective view of a portion of an electrode subassembly formed from an anode having an ALD deposited dielectric layer formed thereon, a separator, and a cathode configured together as a "laminate."

FIG. 5 shows a portion of an electrode subassembly formed from an anode 206, having an ALD deposited dielectric layer formed thereon, a separator 210, and a cathode 204 configured together as a "laminate." These materials can be adhered together by pressing or using any suitable adhesive, for example by using an ion conducting adhesive. The electrode subassembly 200 can be made by adhering an anode 206 and cathode 204 to each side of the separator 210. FIG. 5 specifically shows an electrode subassembly 200 having an cathode/separator/anode/separator/cathode configuration. However, it should be apparent to one of skill in the art that any number of anode, separator and cathode layers or strips of material can be used to form the electrode subassembly 200.

Figure 6:
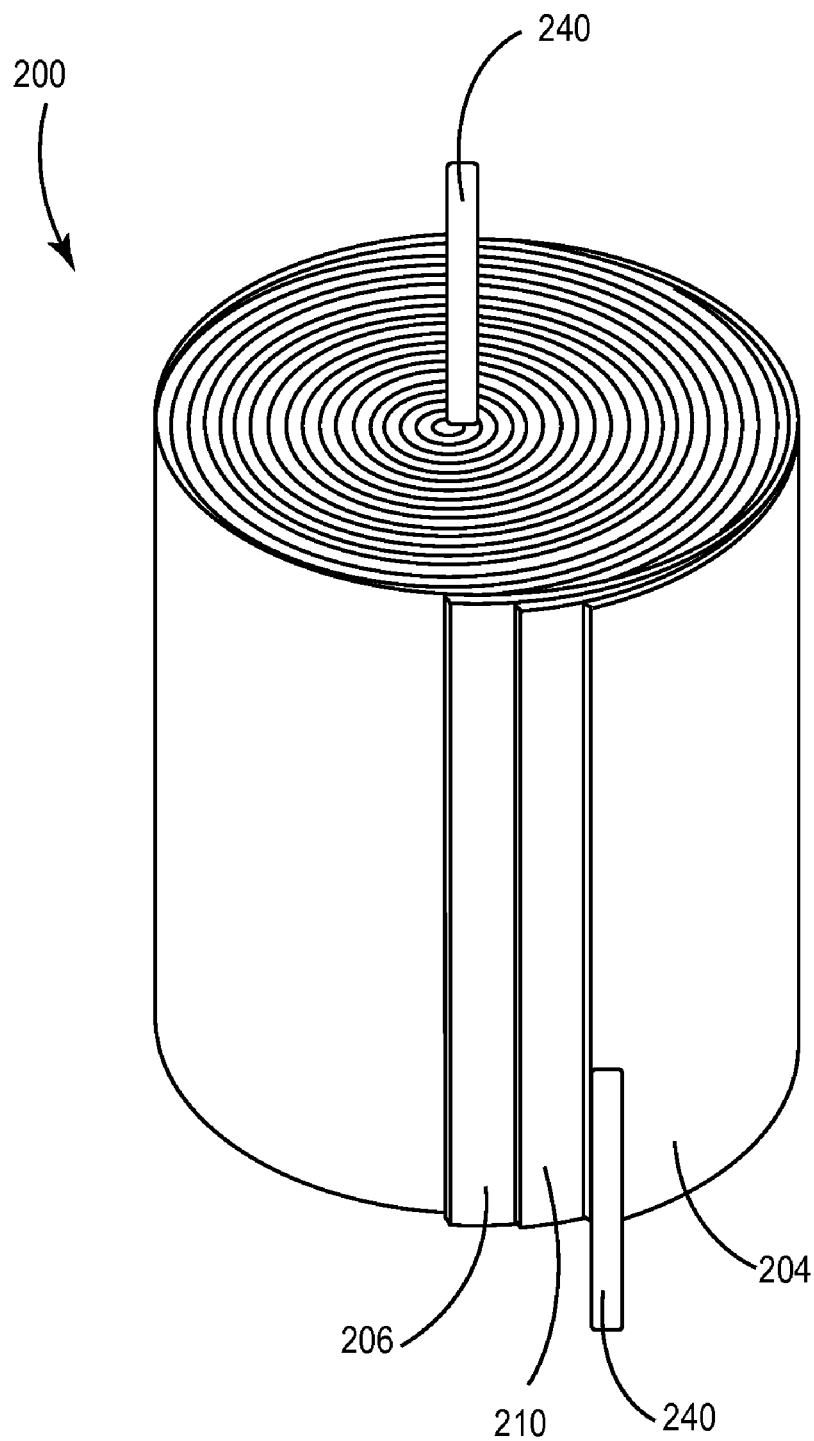
FIG. 6 is a perspective view of the electrode subassembly shown in FIG. 5 wrapped in a cylindrical coil configuration.
Figure 7:
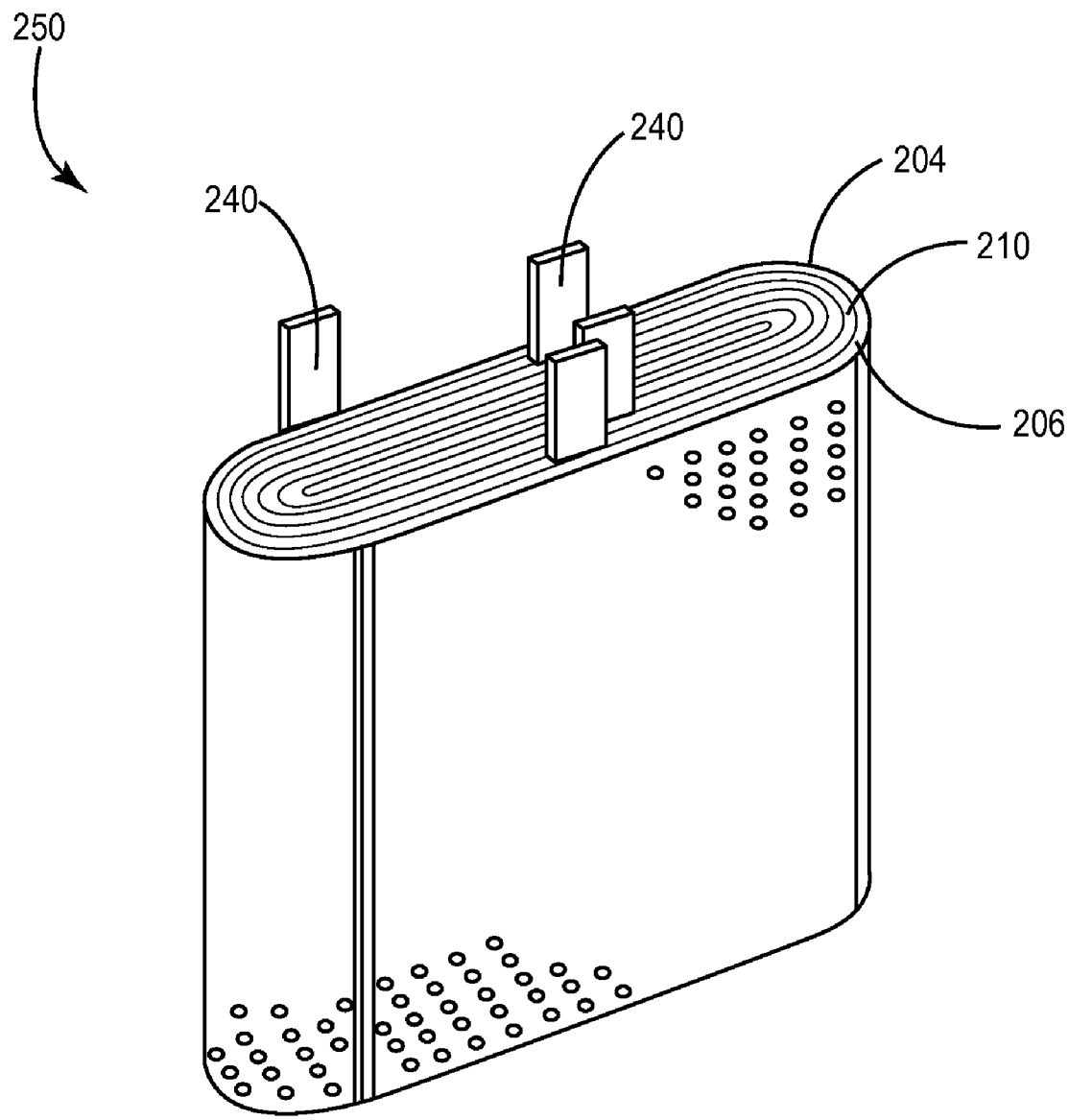
FIG. 7 is a perspective view of an electrode subassembly wrapped in a flat coil configuration.

The electrode subassembly 200 can be coiled or wrapped within the capacitor cell in any suitable configuration. FIG. 6 shows the electrode subassembly 200 wrapped in a cylindrical coil configuration. Electrical connection tabs 240 are shown in FIG. 6, each extending from an anode substrate 106 and cathode 104. The coiled electrode subassembly 200 shown in FIG. 6 is not limited to the generally cylindrical coiled configuration as shown. For example, as shown in FIG. 7, an electrode subassembly 250 is shown wrapped in a flat coil configuration. FIG. 7 also shows electrical connection tabs 240 extending from anode 206 and cathode 204.

Figure 8:
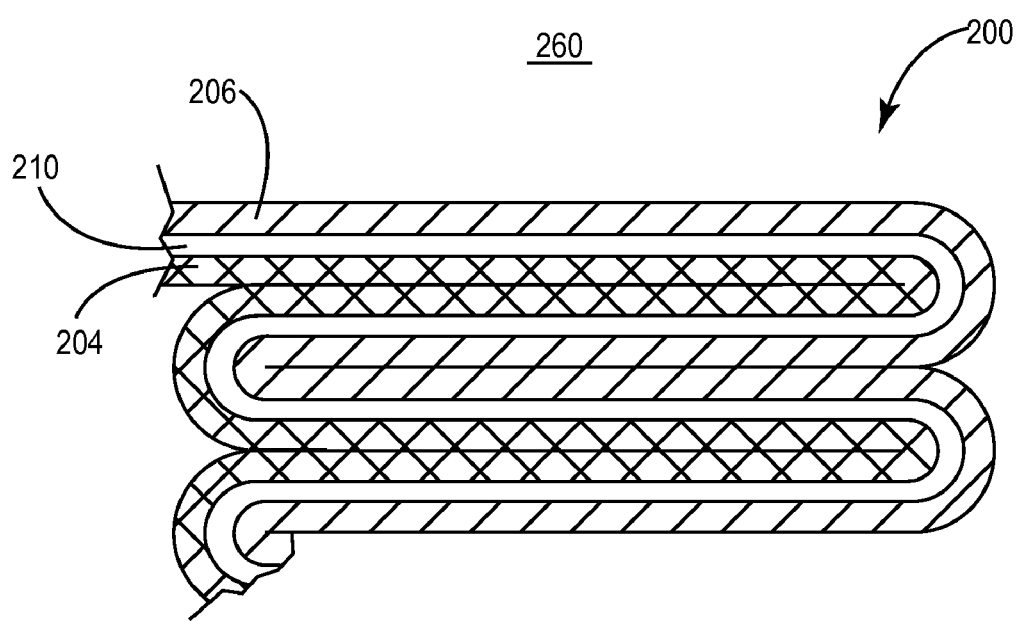
FIG. 8 is a side view of a stacked electrode assembly formed using an anode/separator/cathode laminate subassembly.

Other non-coiled electrode assembly configurations are available. For example, FIG. 8 shows a stacked electrode assembly 260 formed using anode/separator/cathode laminate subassembly 200. The anode/separator/cathode laminate subassembly 200 is stacked by layering the laminate electrode subassembly 200 onto itself in a Z-fold fashion. Stacked configurations of the electrode assembly 260 can contribute to the volume efficiency of a capacitor cell.

Figure 9:
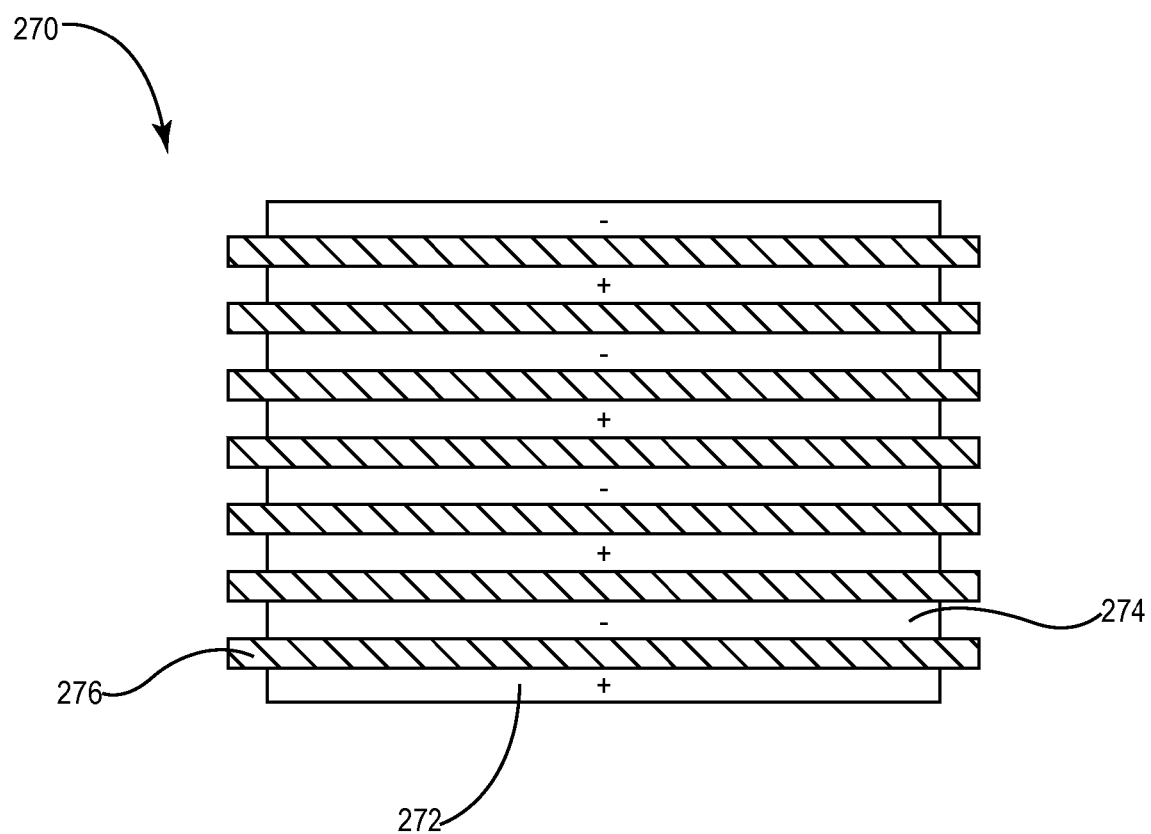
FIG. 9 is a side view an electrode assembly formed by stacking multiple layers of an anode having an ALD deposited dielectric layer, a cathode, and separator.

FIG. 9 shows an electrode assembly 270 formed by stacking multiple layers of anode 272 having an ALD deposited dielectric layer, cathode 274, and separator 276. Each anode 272 and cathode 274 is a substantially rectangularly-shaped segment. However, it should be apparent that anode 272 and cathode 274 can be configured in any suitable shape. The shapes of these layers are primarily a matter of design choice, and are dictated largely by the shape, size, or configuration of the encasement within which the electrode assembly 270 is ultimately disposed. Each anode 272, cathode 274 and separator 276 can be formed into a specific, predetermined shape using die cutting methods or other cutting or forming methods known in the art.

Figure 10:
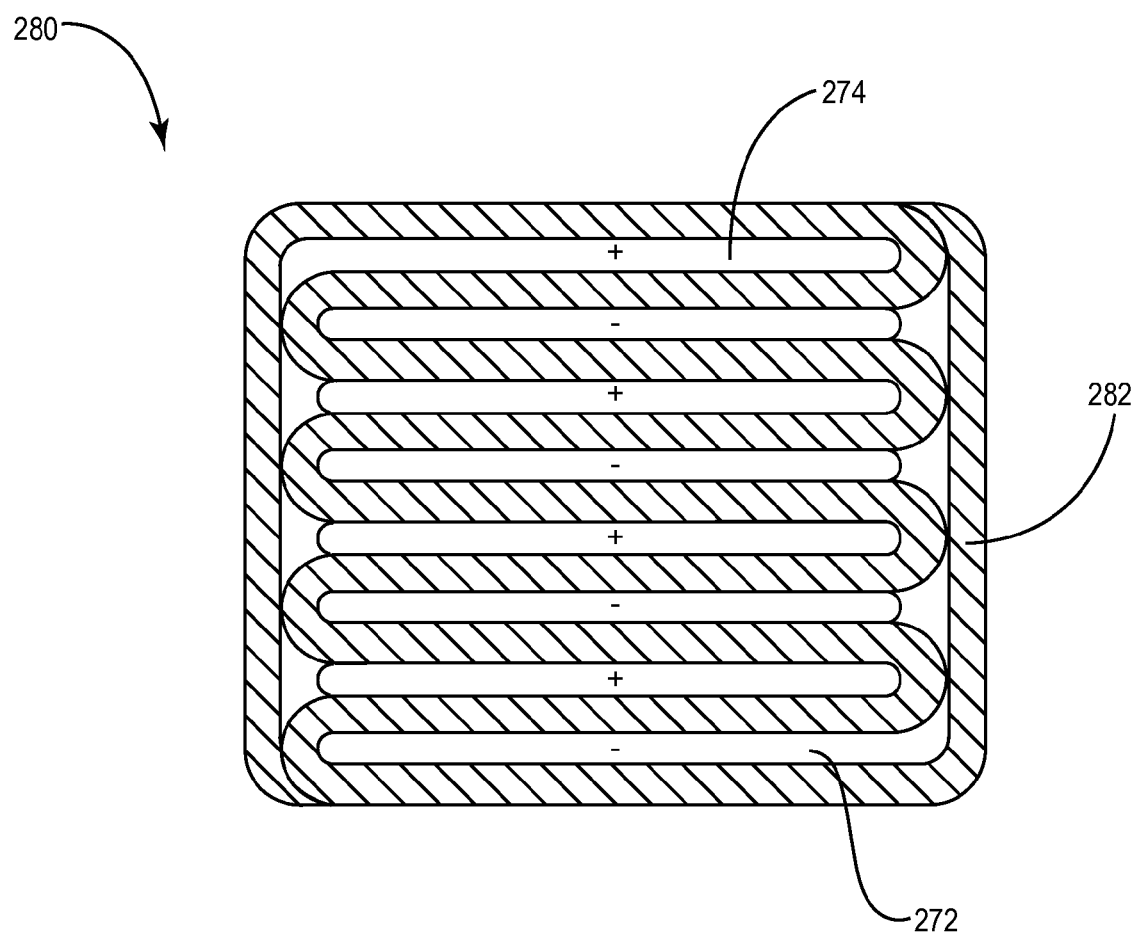
FIG. 10 is a side view of an alternative embodiment of a stacked electrode assembly.

In FIG. 9, separator 276 is configured as substantially rectangularly-shaped segments that are disposed in between each anode 272 and cathode 274. The separator 276 is typically longer than the anode 272 and cathode 274 to ensure that proper separation of anode 272 and cathode 274 is maintained. Alternatively, as shown in FIG. 10, a separator 282 is configured as one long strip of material that is wrapped around the stacked electrodes 272 and 274 to form electrode assembly 280. In the embodiments described herein, the anodes and cathodes are generally shown as a single layer of material. It is recognized that in certain embodiments, one or more of the anode layers and cathode layers in a stacked or coiled electrode assembly may include multiple layers.

It should also be understood by skilled artisan that the length of the anode/separator/cathode laminate used or that the precise number of anode and cathode layers selected for use in a given capacitor cell will depend on the energy density, volume, voltage, current, energy output and other requirements of the device. Similarly, it will be understood that the precise number connector tabs and their locations and methods for coupling electrode layers together will depend on particular requirements placed upon the capacitor cell in a given application.

Figure 11:
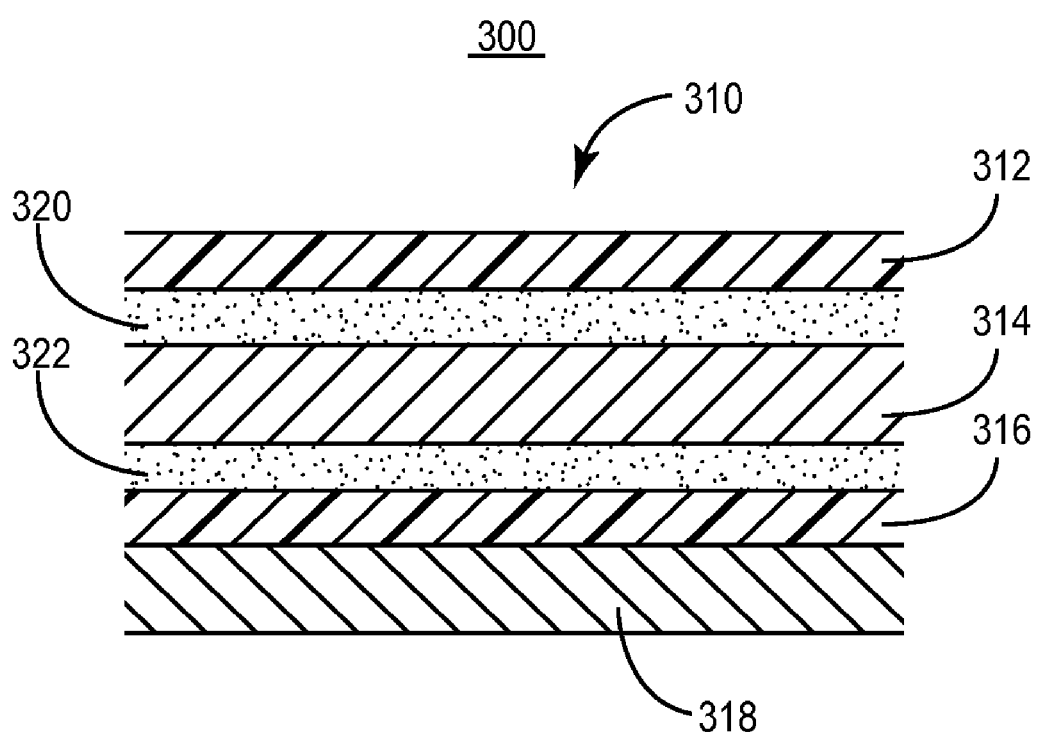
FIG. 11 is a sectional view of a portion of solid electrolytic capacitor cell.

FIG. 11 is a sectional view of a portion of solid electrolytic capacitor cell 300. A laminate structure 310 includes anode substrate 314 upon which dielectric layers 320 and 322 have been deposited using ALD methods. Anode substrate 314 may be in the form of a foil or sheet and may be etched or otherwise surface-area enhanced. In alternative embodiments, anode substrate may be a porous slug. Solid electrolyte 312 and 316 is disposed over the dielectric layers 320 and 322. A cathode layer 318 is provided, separated from the anode substrate 314 by the dielectric layer 322 and the solid electrolyte 316. The cathode layer 318 may be any suitable cathodic material, including a metal or metal alloy and may include an ALD formed dielectric coating.

The solid electrolyte 312 and 314 is generally a thin layer and may be composed of a solid solution of a metal salt and a polymer, e.g., a solid solution of an alkali metal salt and a polymer including polytetraethylene glycol, polyacrylonitrile, polyvinyl pyrrolidine, diacrrylate, or mixtures thereof. The solid solution can be formed using a liquid solvent, such as ethylene carbonate. The solid electrolyte layers 312 and 314 could be prepared in sheets and laid onto the dielectric layers 320 and 322. Alternatively solid electrolyte layers 312 and 314 may be deposited on the dielectric layers 320 and 322 in a non-solid solution and allowed to cure as a film over the dielectric layers 320 and 322. Examples of solid electrolytes for use in a layered capacitor are generally disclosed in U.S. Pat. No. 5,646,815 issued to Owens, et al., hereby incorporated herein by reference in its entirety. Other configurations of solid state capacitors are not outside the scope of the invention such as chip type capacitors.

Figure 12:
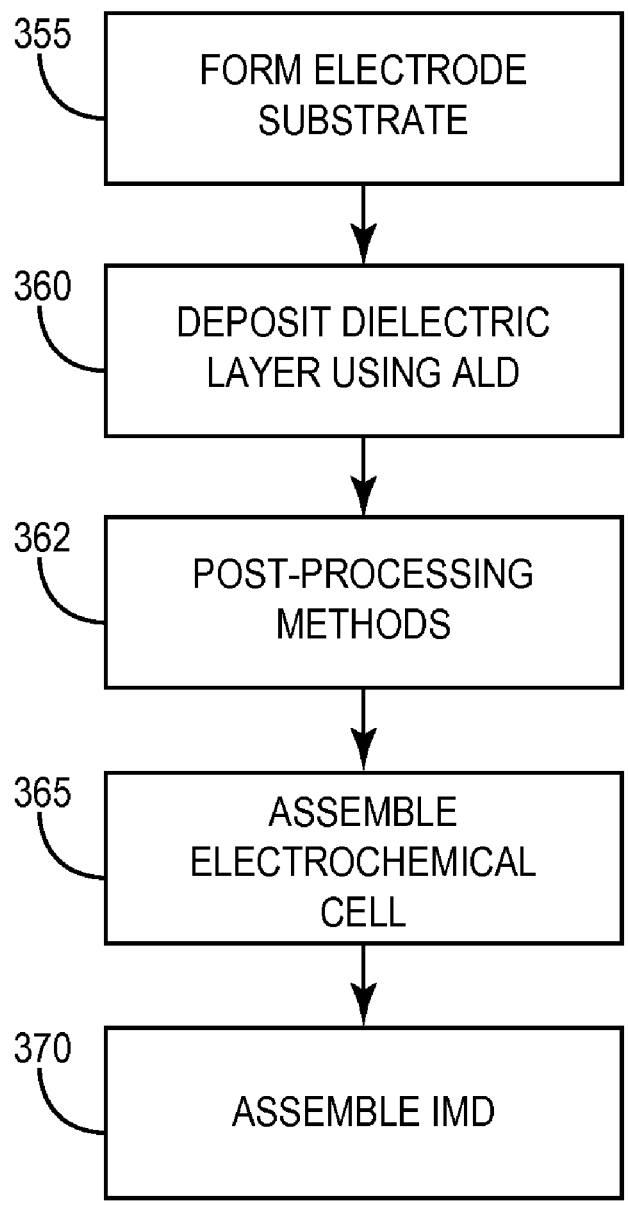
FIG. 12 is a flow chart summarizing a method for manufacturing an electrolytic capacitor cell having a dielectric layer formed using ALD.

FIG. 12 is a flow chart summarizing a method 300 for manufacturing a capacitor cell having a dielectric layer formed using ALD. At block 355, an electrode substrate is formed. At block 360, a dielectric layer is deposited on the electrode substrate using ALD. At block 362, optional post-processing methods are performed such as thermal treatments to alter the structure of the ALD deposited layer or electrochemical anodization methods. At block 365, the electrode is assembled with other components in a capacitor cell. At block 370, the capacitor cell is assembled with other components, such as other electrochemical cells and a hybrid circuit board, in the housing of an IMD.

Thus, an electrolytic capacitor cell for use in medical devices has been presented in the foregoing description with reference to specific embodiments. It is appreciated that various modifications to the referenced embodiments may be made without departing from the scope of the invention as set forth in the following claims.

The invention claimed is:

1. An implantable medical device comprising:
a high voltage electrolytic capacitor cell that includes:
a first electrode substrate that comprises a valve metal;
a dielectric layer formed on the electrode substrate by atomic layer deposition; and
a solid electrolyte in contact with the dielectric layer.

2. The cell of claim 1 wherein the first electrode substrate includes one of: a metal, a metal alloy, and a multi-phase metal alloy.

3. The cell of claim 1 wherein the first electrode substrate is a surface area enhanced substrate.

4. The cell of claim 1 wherein the dielectric layer includes a plurality of first atomic monolayers formed of an oxide of at least one first metal.

5. The cell of claim 4 wherein the dielectric layer includes a plurality of second atomic monolayers formed of an oxide of at least one second metal.

6. The cell of claim 5 wherein the first and second atomic monolayers are formed as alternating layers.

7. The cell of claim 1 wherein the dielectric layer includes a plurality of atomic monolayers wherein each monolayer includes a first oxide of a first metal and a second oxide of a second metal.

8. The cell of claim 1 wherein the first electrode substrate is an anode substrate.

9. The cell of claim 1 wherein the dielectric layer is processed subsequent to the atomic layer deposition.

10. The cell of claim 9 wherein the processing includes one of annealing and electrochemical anodization following the atomic layer deposition.

11. A method for manufacturing an electrolytic capacitor cell for use in an implantable medical device, comprising:
forming an electrode substrate;
depositing a dielectric layer on the electrode substrate using atomic layer deposition;
contacting a solid electrolyte with the dielectric layer; and
assembling the electrode substrate in the capacitor cell for use in an implantable medical device.

12. The method of claim 11 wherein the electrode substrate is formed from one of: a metal, a metal alloy, a multi-phase metal alloy, and a ceramic.

13. The method of claim 11 wherein forming the electrode substrate includes enhancing the surface area of the electrode substrate.

14. The method of claim 11 wherein depositing the dielectric layer includes depositing a first plurality of atomic monolayers of an oxide of at least one first metal.

15. The method of claim 14 wherein depositing the dielectric layer includes depositing a second plurality of atomic monolayers of an oxide of at least one second metal.

16. The method of claim 15 wherein the first plurality of atomic monolayers and the second plurality of atomic monolayers are deposited in an alternating manner.

17. The method of claim 11 wherein depositing the dielectric layer includes depositing a plurality of the atomic monolayers wherein each monolayer includes a first oxide of a first metal and a second oxide of a second metal.

18. The method of claim 11 wherein the electrode substrate is an anode substrate.

19. The method of claim 11, further including performing a processing method for treating the dielectric layer subsequent to depositing the dielectric layer.

20. The method of claim 19 wherein the processing method includes one of annealing and electrochemical anodization.

21. An implantable medical device comprising an electrolytic capacitor cell wherein the capacitor cell comprises:
an anode electrode substrate;
a dielectric layer formed on the anode electrode substrate using atomic layer deposition; and
a solid electrolyte in contact with the dielectric layer.

22. The implantable medical device of claim 1, wherein the first electrode substrate comprises one of aluminum, niobium, titanium, tantalum, and zirconium.

23. The implantable medical device of claim 1, wherein the dielectric layer comprises one of tantalum oxide, niobium oxide, aluminum oxide, chromium oxide, zirconium oxide, zinc oxide, vanadium oxide, hafnium oxide, and titanium oxide.

24. The implantable medical device of claim 1, wherein the dielectric layer comprises tantalum oxide.

25. An implantable medical device comprising:
a high voltage electrolytic capacitor cell that includes:
an anode electrode substrate that comprises aluminum;
a dielectric layer formed on the electrode substrate by atomic layer deposition, the dielectric layer comprises tantalum pentoxide ($Ta_2O_5$); and
a solid electrolyte in contact with the dielectric layer.

* * * * *